United States Patent
Mantell et al.

(10) Patent No.: US 8,955,511 B2
(45) Date of Patent: *Feb. 17, 2015

(54) METHOD AND APPARATUS FOR HUMIDIFICATION AND WARMING OF AIR

(75) Inventors: Robert R. Mantell, Arlington Heights, IL (US); Peter A. Manzie, Berwyn, IL (US)

(73) Assignee: Northgate Technologies, Inc., Elgin, IL (US)

( * ) Notice: Subject to any disclaimer, the term of this patent is extended or adjusted under 35 U.S.C. 154(b) by 406 days.

This patent is subject to a terminal disclaimer.

(21) Appl. No.: 13/216,602

(22) Filed: Aug. 24, 2011

(65) Prior Publication Data

US 2011/0306925 A1 Dec. 15, 2011

Related U.S. Application Data

(63) Continuation of application No. 12/627,454, filed on Nov. 30, 2009, now Pat. No. 8,091,546, which is a continuation of application No. 11/248,412, filed on Oct. 12, 2005, now Pat. No. 7,647,925, which is a continuation of application No. 09/896,821, filed on Jun. 29, 2001, now Pat. No. 6,976,489.

(60) Provisional application No. 60/215,442, filed on Jun. 30, 2000.

(51) Int. Cl.
*A61M 11/00* (2006.01)
*A61M 13/00* (2006.01)

(52) U.S. Cl.
CPC ..... *A61M 13/003* (2013.01); *A61M 2205/3368* (2013.01); *A61M 2206/14* (2013.01); *Y10S 261/65* (2013.01)
USPC 128/203.16; 261/101; 261/104; 261/DIG. 65

(58) Field of Classification Search
USPC ............. 128/201.13, 203.16, 203.17, 204.13, 128/204.17; 261/101, 104, DIG. 65, 154, 261/129, 130
See application file for complete search history.

(56) References Cited

U.S. PATENT DOCUMENTS

| | | |
|---|---|---|
| 1,682,344 A | 8/1928 | Lesieur |
| 2,408,136 A | 9/1946 | Fox |

(Continued)

FOREIGN PATENT DOCUMENTS

| | | |
|---|---|---|
| AU | 74564/74 | 4/1976 |
| DE | 2834622 C2 | 8/1978 |

(Continued)

OTHER PUBLICATIONS

Notification of Reason for Rejection directed against Japanese Patent Application No. 2002-505064, dated Dec. 21, 2010 (2 pgs.).

(Continued)

*Primary Examiner* — Steven Douglas
(74) *Attorney, Agent, or Firm* — Brinks Gilson & Lione

(57) ABSTRACT

A gas apparatus for use in a medical procedure may include a housing, a heater, a port, and a dispensing device. The housing defines a chamber having a gas inlet and a gas outlet. The heater warms a gas flowing through the chamber. The port is positioned in fluid communication with the chamber. The dispensing device is inserted within the port for delivering water in aerosol form to warmed gas as it exits the gas outlet.

14 Claims, 6 Drawing Sheets

(56) References Cited

U.S. PATENT DOCUMENTS

| | | |
|---|---|---|
| 2,579,113 A | 12/1951 | Gardner |
| 2,830,580 A | 4/1958 | Saklad et al. |
| 3,481,323 A | 12/1969 | Cook et al. |
| 3,532,270 A | 10/1970 | Schoen, Jr. |
| 3,563,381 A | 2/1971 | Edelson et al. |
| 3,582,717 A | 6/1971 | Perlaky |
| 3,659,604 A | 5/1972 | Melville et al. |
| 3,674,010 A | 7/1972 | Falenks |
| 3,712,298 A | 1/1973 | Snowdon et al. |
| 3,735,559 A | 5/1973 | Salemme |
| 3,747,598 A | 7/1973 | Cowans |
| 3,782,363 A | 1/1974 | Davis |
| 3,809,374 A | 5/1974 | Schossow |
| 3,870,072 A | 3/1975 | Lindemann |
| 3,871,371 A | 3/1975 | Weigl |
| 3,885,590 A | 5/1975 | Ford et al. |
| 3,897,682 A | 8/1975 | Brooks |
| 3,904,849 A | 9/1975 | Lucero et al. |
| 3,912,795 A | 10/1975 | Jackson |
| 3,952,609 A | 4/1976 | Klemm |
| 3,954,920 A | 5/1976 | Heath |
| 3,961,626 A | 6/1976 | Houchen et al. |
| 3,982,095 A | 9/1976 | Robinson |
| 3,982,533 A | 9/1976 | Wiest |
| 4,010,748 A | 3/1977 | Dobritz |
| 4,048,992 A | 9/1977 | Lindemann et al. |
| 4,054,622 A | 10/1977 | Lester |
| 4,063,548 A | 12/1977 | Klatt et al. |
| 4,086,305 A | 4/1978 | Dobritz |
| 4,092,635 A | 5/1978 | Warner |
| 4,101,294 A | 7/1978 | Kimura |
| 4,101,611 A | 7/1978 | Williams |
| 4,110,419 A | 8/1978 | Miller |
| 4,121,583 A | 10/1978 | Chen |
| 4,201,737 A | 5/1980 | Carden |
| 4,207,887 A | 6/1980 | Hiltebrandt et al. |
| 4,215,681 A | 8/1980 | Zalkin et al. |
| 4,225,542 A | 9/1980 | Wall et al. |
| 4,256,100 A | 3/1981 | Levy et al. |
| 4,276,128 A | 6/1981 | Nishino et al. |
| 4,285,245 A | 8/1981 | Kennedy |
| 4,288,396 A | 9/1981 | Ottestad |
| 4,303,601 A | 12/1981 | Grimm et al. |
| 4,355,636 A | 10/1982 | Oetjen et al. |
| 4,360,017 A | 11/1982 | Barlett |
| 4,369,777 A | 1/1983 | Lwoff et al. |
| 4,381,267 A | 4/1983 | Jackson |
| 4,401,114 A | 8/1983 | Lwoff et al. |
| 4,430,994 A | 2/1984 | Clawson et al. |
| 4,441,027 A | 4/1984 | Richardson et al. |
| 4,464,169 A | 8/1984 | Semm |
| 4,519,587 A | 5/1985 | Peckels et al. |
| 4,532,088 A | 7/1985 | Miller |
| 4,589,409 A | 5/1986 | Chatburn et al. |
| 4,612,434 A | 9/1986 | Ianitelli et al. |
| 4,621,632 A | 11/1986 | Bartels et al. |
| 4,621,633 A | 11/1986 | Bowles et al. |
| 4,652,408 A | 3/1987 | Montgomery |
| 4,657,713 A | 4/1987 | Miller |
| 4,670,006 A | 6/1987 | Sinnett et al. |
| 4,674,494 A | 6/1987 | Wiencek |
| 4,676,774 A | 6/1987 | Semm et al. |
| 4,686,974 A | 8/1987 | Sato et al. |
| 4,708,831 A | 11/1987 | Elsworth et al. |
| 4,714,078 A | 12/1987 | Paluch |
| 4,715,372 A | 12/1987 | Philippbar et al. |
| 4,715,998 A | 12/1987 | Clow |
| 4,735,603 A | 4/1988 | Goodson et al. |
| 4,747,403 A | 5/1988 | Gluck et al. |
| 4,748,314 A | 5/1988 | Desage |
| 4,770,168 A | 9/1988 | Rusz et al. |
| 4,773,410 A | 9/1988 | Blackmer et al. |
| 4,773,411 A | 9/1988 | Downs |
| 4,825,863 A | 5/1989 | Dittmar et al. |
| 4,830,849 A | 5/1989 | Osterholm |
| 4,874,362 A | 10/1989 | Wiest et al. |
| 4,921,642 A | 5/1990 | La Torraca |
| 4,966,578 A | 10/1990 | Baier et al. |
| 5,006,109 A | 4/1991 | Douglas et al. |
| 5,013,294 A | 5/1991 | Baier |
| 5,062,145 A | 10/1991 | Zwaan et al. |
| 5,098,375 A | 3/1992 | Baier |
| 5,109,471 A | 4/1992 | Lang |
| 5,139,478 A | 8/1992 | Koninckx et al. |
| 5,144,474 A | 9/1992 | Keable et al. |
| 5,148,801 A | 9/1992 | Douwens et al. |
| 5,179,966 A | 1/1993 | Losee et al. |
| 5,192,499 A | 3/1993 | Sakai et al. |
| 5,195,514 A | 3/1993 | Liu et al. |
| 5,195,515 A | 3/1993 | Levine |
| 5,246,419 A | 9/1993 | Absten |
| 5,318,731 A | 6/1994 | Yokoya et al. |
| 5,349,946 A | 9/1994 | McComb |
| 5,367,604 A | 11/1994 | Murray |
| 5,411,474 A | 5/1995 | Ott et al. |
| 5,435,298 A | 7/1995 | Anthony |
| 5,460,172 A | 10/1995 | Eckerbom et al. |
| 5,482,031 A | 1/1996 | Lambert |
| 5,769,071 A | 6/1998 | Turnbull |
| 5,906,201 A | 5/1999 | Nilson |
| 5,964,223 A | 10/1999 | Baran |
| 6,010,118 A | 1/2000 | Milewicz |
| 6,014,890 A | 1/2000 | Breen |
| 6,039,696 A | 3/2000 | Bell |
| 6,068,609 A | 5/2000 | Ott et al. |
| 6,095,505 A | 8/2000 | Miller |
| 6,102,037 A | 8/2000 | Koch |
| 6,394,084 B1 | 5/2002 | Nitta |
| 6,397,842 B1 | 6/2002 | Lee |
| 6,510,848 B1 | 1/2003 | Gibertoni |
| 6,550,476 B1 | 4/2003 | Ryder |
| 6,814,714 B1 | 11/2004 | Novak et al. |

FOREIGN PATENT DOCUMENTS

| | | |
|---|---|---|
| DE | 2810325 A1 | 9/1979 |
| DE | 3139135 C2 | 10/1981 |
| DE | 3430541 A1 | 8/1984 |
| DE | 3615611 C2 | 5/1986 |
| DE | 3927594 A1 | 8/1989 |
| DE | 3932766 A1 | 9/1989 |
| DE | 195 10710 A1 | 3/1995 |
| DE | 19923297 A1 | 12/1999 |
| EP | 0169151 B1 | 7/1988 |
| EP | 0274868 A1 | 7/1988 |
| EP | 0311238 A1 | 4/1989 |
| EP | 0350499 B1 | 4/1993 |
| EP | 0567158 A2 | 10/1993 |
| EP | 0533644 B1 | 12/1996 |
| EP | 0569241 B1 | 12/1999 |
| EP | 1005878 A1 | 6/2000 |
| EP | 1005878 A3 | 3/2001 |
| EP | 0387220 B2 | 4/2001 |
| FR | 2276065 | 1/1976 |
| FR | 2636845 A1 | 3/1990 |
| GB | 729352 | 5/1955 |
| GB | 2173108 A | 10/1986 |
| GB | 2 338 420 | 12/1999 |
| JP | 1990-118555 | 9/1990 |
| JP | 2000-24109 | 1/2000 |
| JP | 199650029 | 12/2010 |
| NL | 8702698 | 6/1989 |
| WO | WO 87/01443 A1 | 3/1987 |
| WO | WO 89/04188 A1 | 5/1989 |
| WO | WO 91/19527 | 12/1991 |
| WO | 94/02192 | 2/1994 |
| WO | WO 94/28952 | 12/1994 |
| WO | WO 98/26826 | 6/1998 |

OTHER PUBLICATIONS

Karrer, W. *Pillars of therapy of chronic obstructive bronchitis*, Schweiz Rundsch Med Prax. 1989 Feb. 7, 78(6): 121-5, Germany.

(56) References Cited

OTHER PUBLICATIONS

Kimmel, W. and Gerke D., *EMI Regulations and Medial Device Design*, National Library of Medicine, Sep. 10, 1992.
Colvin, D., *Designing Resuable Interconnectors for Minimally Invasive Surgery*, National Library of Medicine, Sep. 10, 1992.
*Leitfaden and Atlas der Laparoskopie*, W. Siede and H. Schneider, J.F. Lehmanns Verlag Müchen, 1962 (with partial translation), 6 pages.
*The persufflator: an insufflations device for laparoscopy and especially for $CO_2$—laser-endoscopic surgery*, P. Koninckx and E. Vandermeershc, 1991, 3 pages.
V.N. Dolorico et al., "A Safe Nonbreathing System: Humidity, Sterility, Cost" Anesthesia and Analgesia . . . Current Researches, vol. 53, No. 1, Jan.-Feb. 1974, pp, 75-79.
G.C. Grant et al., "A New Humidifier" Anesthesia and Intensive Care, vol. IV, No. 3, Aug. 1976, pp. 205-210.
Jack Chalon et al., "Humidification in a Modified Circle System" Anesthesia and Analgesia, vol. 56, No. 3, May-Jun. 1979, pp. 216-220.
P. Whitehurst et al., "Temperature Alarm and Cut-Out System for Use with Heated Water Humidifiers" British Journal of Anesthesia, vol. 52, 1980, pp. 557-558.
Thomas J. Poulton et al., "Humidification of Rapidly Flowing Gas" Critical Care Medicine, vol. 9, No. 1, Jan. 1981, pp. 59-63.
Wolf D. Seufert et al., "The Liquid Barrier Filter—A New Concept to Eliminate Particulate Contaminants from Gases" Health Physics, vol. 42, No. 2, Feb. 1982, pp. 209-216.
M. Ogino et al., "Moisture-Conserving Efficiency of Condenser Humidifiers" Anaesthesia, vol. 40, 1985, pp. 990-995.
Douglas E. Ott, "Contamination via Gynecologic Endoscopy Insufflation" Journal of Gynecologic Surgery, vol. 5, No. 2, 1989, pp. 205-208.
Douglas E. Ott, "Laparoscopic Hypothermia" Journal of Laparoendoscopic Surgery, vol. 1, No. 3, 1991, pp. 127-131.
Douglas E. Ott, "Correction of Laparoscopic Insufflation Hypothermia" Journal of Laparoendoscopic Surgery, vol. 1, No. 4, 1991, pp. 183-186.
"Computerized Insufflation—New Levels of performance, Safety and Simplicity, " Salesman Leaflet published by Snowden Pencer USA, 1992, two pages.
"Accessories for Thermoflator Moisturizing System for CO2 Gas," Salesman Leaflet published by Karl Storz-Endoskope, 1994, one page.
J.R. Bessell et al., "Hypothermia Induced by Laparoscopic Insufflation," Surgical Endoscopy, vol. 9, 1995, pp. 791-796.
M.L. Texler et al., "Tumour Cell Movement During Heating and Humidification of Insufflating C02: An In Vitro Model," Aust, N.Z. J. Surg., vol. 68,1998, pp. 740-741.
W.G. Mouton et al., "Adelaide Trial Demonstrates Significant Reduction of Post-Operative Pain When Using Heated and Humidified C02," Cook Medical Technology Technological Observer, Jan. 1998, pp. 1-4 and two additional pages.
D.E. Ott et al., "Reduction of Laparoscopic-Induced Hypothermia, Postoperative Pain and Recovery Room Length of Stay by Pre-Conditioning Gas with the Insuflow Device: A Prospective Randomized Controlled Multi-Center Study," Journal of the Society of Laparoscopic Surgeons, vol. 2, 1998, pp. 321-329.
J.R. Bessell et al., "Influence of Gas Temperature During Laparoscopic Procedures," published by Springer in "the Pathophysiology of Pneumoperitoneum" edited by R. Rosenthal et al., 1998, pp. 18-27.
J.R. Bessell et al., "Humidified Gas Prevents Hypothermia Induced by Laparoscopic Insufflation—A Randomized Controlled Study in a Pig Model," Surgical Endoscopy, vol. 13, 1999, pp. 101-104.
W.G. Mouton et al., "A Randomized Controlled Trial Assessing the Benefit of Humidified Insufflation Gas During Laparascopic Surgery," Surgical Endoscopy, vol. 13, 1999, pp. 106-108.
W.G. Mouton et al., "A Randomized Controlled Trial to Determine the Effects of Humidified Carbon Dioxide Insufflation During Thoracoscopy," Surgical Endoscopy, vol. 13, 1999, pp. 382-385.
W.G. Mouton et al., "Pain after Laparoscopy," Surgical Endoscopy, vol. 13, 1999, pp. 445-448.
J. Volz et al., "Characteristic Alterations of the Peritoneum after Carbon Dioxide Pneumoperitoneum," Surgical Endoscopy, vol. 13, 1999, pp. 611-614.
A.R. Biegner et al., "Quantification of Insensible Water Loss Associated with Insufflation of Nonhumidified C02 in Patients Undergoing Laparascopic Surgery," Journal of Laparoendoscopic & Advances Surgical Techniques, vol. 9, No. 4, 1999, pp. 325-329.
S. Worcester, "Adhesions May Cause Pain in Some Women," Ob. Gyn, News, Jun. 1, 1999, one page.
V.R. Jacobs et al., "Measurement of C02 Hypothermia During Laparoscopy and Pelviscopy: How cold It Gets and How to Prevent It," The Journal of the American Associate of Gynecologic Laparoscopists, vol. 6, No. 3, Aug. 1999, pp. 289-295.
"Safety in Laparoscopy, from the World Congress on Genecologisc Endoscopy and the t" Annual Meeting of the Israel Society of Gynecological Endoscopy, 2000 and made publicly available by OBGYN. net at http://www.obqyn.net/displaytranscript.asp?page=/avtranscripts/isreal2k turner as of Apr. 6, 2004, 1999, three pages.
M.A. Raymond et al., "Feasibility of Therapeutic Pneumomperotoneum in a Large Animal Model Using a Microvaporsiator," Surgical Endoscopy: Ultrasound and Interventional Techniques, 2000, five pages.
"Insuflow" webpage, made publicly available by Georgia Biomedical at http://www.georgiabiomedical.com/heathydr,htm as of Sep. 14, 2000, one page.
"Controller Circuit & AC/DC Converter" webpage, made publicly available by Biomedical at http://www.georgiabiomedical.com/controller,htm as of Sep. 14, 2000, one page.
"There is a Difference" webpage, made publicly available by Georgia Biomedical http://www.qeorqiabiomedical.com/insuflow,htm as of Sep. 14, 2000, one page.
"Therme-Pneu Computer—Op-Pneu Computer," Salesman Leaflet published by WISAP, while the date of publication is unknown, it is believed that the leaflet was published prior to Jun. 30, 2000, two pages.
"Semm System," Salesman Leaflet published by WISAP, white the date of publication is unknown, it is believed that the leaflet was published prior to Jun. 30, 2000, four pages.
Victor Gomel, MD., Foreward of the book entitled"Peritoneal Surgery," by Gere S. DiZerega, MD., publisher unknown, while the date of publication is unknown it is believed that the Foreward was published prior to Jun. 30, 2000, pp. vii to xi.
Abstract of A.R. Biegner et al., "Quantification of Insensible Water Loss Associated with Insufflation of Nonhumidified C02 in Patients Undergoing Laparascopic Surgery," Journal of Laparoendoscopic & Advanced publicly available by PubMed at file://C://WINDOWS/TemporaryInternetFiles/OLKB161/Entrez-PubMed.htm as of Apr. 5, 2004, one page.
Abstract of J.R. Bessell et al., "Humidified Gas Prevents Hypothermia Induced by Laparascopic Insufflation—a Randomized controlled Study in a Pig Model," Surgical Endoscopy, 1999 pp. 101-104, made publicly available by PubMed at file://C://Windows//TemporaryInternetFiles/OLKb161/Entrez-PubMed.htm as of Apr. 5, 2004, one page
M. Korell et al., "Pain Intensity Following Laparoscopy," Surgical Laparoscopy vol. 6, No. 5, 1996, pp. 375-379.
Abstract of J.R. Bessell et al., "A Randomized Controlled Trial Assessing the Benefit of Humidified Insufflation Gas During Laparascopic Surgery," Surgical Endoscopy, vol. 13, 1999, pp. 106-108, made publicly available by PubMed at file://C:/WINDOWS/Temporary_Internet_Files/OLKB161/Entrez-PubMed.htm as of Apr. 5, 2004, one page.
Siede, Dr. Werner et al., "Leitfaden und Atlas der Laparoskopie", J.F. Lehmanns Verlag Munchen (abbreviated translation attached)., no date.
Koninckx, Philippe R. et al., "The persufflator: an insufflations device for laparoscopy and especially for CO2-laser-endoscopic surgery", Human Reproduction, vol. 6, No. 9, pp. 128-129, 1991.
Translation of the Office Action—Decision of Refusal and Decision to Dismiss the Amendment directed against Japanese Patent Application No. 2002-505064, dated Aug. 20, 2012, 3 pages.
English Translation of Notification of Reason for Rejection (Final) directed against Japanese Patent Application No. 2002-505064, dated Nov. 8, 2011 (2 pgs.).

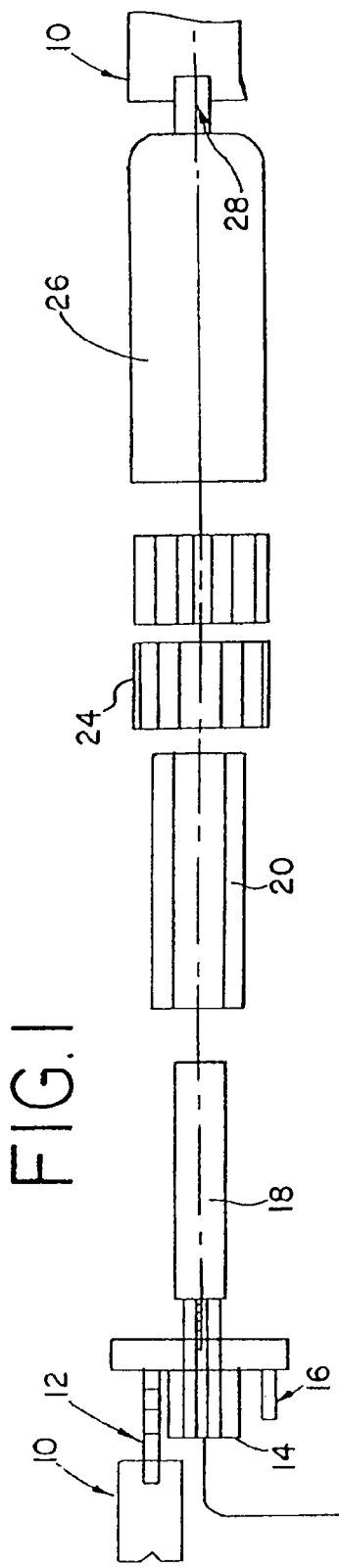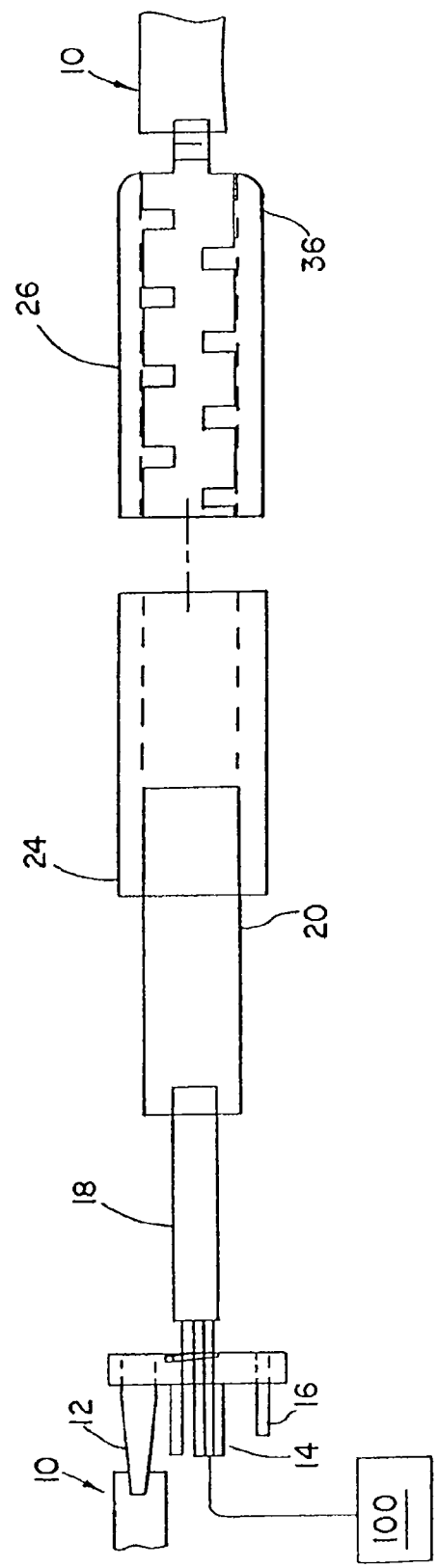

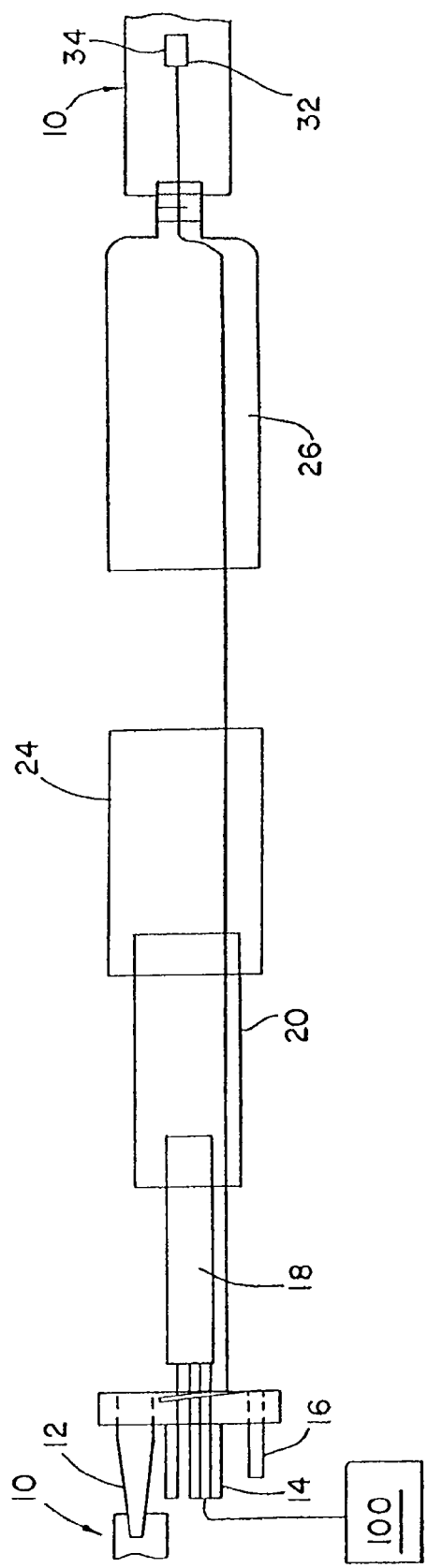
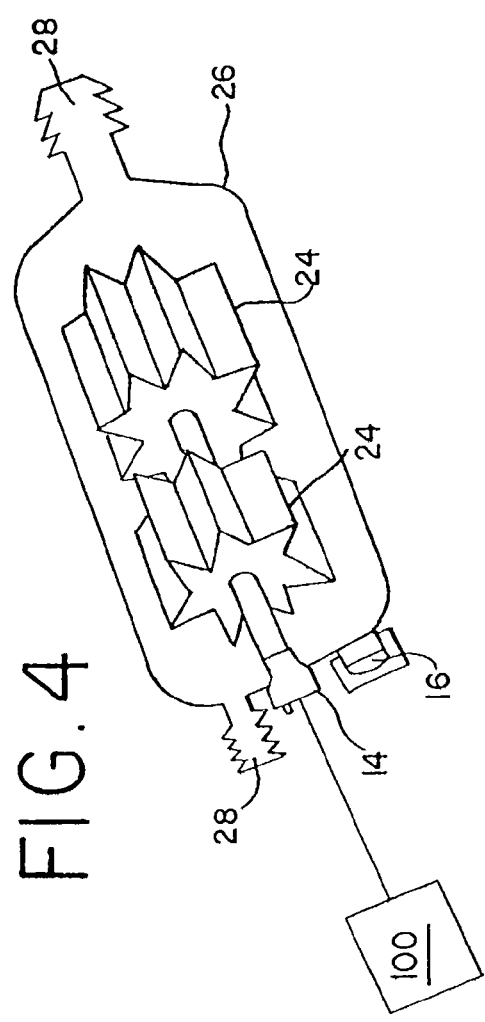

METHOD AND APPARATUS FOR HUMIDIFICATION AND WARMING OF AIR

RELATED APPLICATIONS

The present application is a continuation of U.S. patent application Ser. No. 12/627,454, filed Nov. 30, 2009 now U.S. Pat. No. 8,091,546, which is a continuation of U.S. patent application Ser. No. 11/248,412 (now U.S. Pat. No. 7,647,925), filed Oct. 12, 2005, which is a continuation of U.S. patent application Ser. No. 09/896,821 (now U.S. Pat. No. 6,976,489), filed Jun. 29, 2001, which claims priority to U.S. Provisional Pat. App. No. 60/215,442, filed Jun. 30, 2000, the entirety of each of which are hereby incorporated by reference.

The present application is related to U.S. patent application Ser. No. 11/649,641 (now U.S. Pat. No. 7,762,251), filed Jan. 4, 2007, which is a continuation of U.S. patent application Ser. No. 11/248,412 (still pending), filed Oct. 12, 2005, which is a continuation of U.S. patent application Ser. No. 09/896,821 (now U.S. Pat. No. 6,976,489), filed Jun. 29, 2001, which claims priority to U.S. Provisional Pat. App. No. 60/215,442, filed Jun. 30, 2000, the entirety of each of which are hereby incorporated by reference.

BACKGROUND

1. Field of the Invention

The present invention relates to an apparatus and method used to humidify and/or warm a gas prior to its use in a surgical or other medical procedure.

2. Discussion of Related Art

Many medical and surgical procedures require the supply to a patient of warmed and/or humidified gas at constant high flow rates. Ideally, the flow rate should be approximately 20 liters per minute, the relative humidity should be approximately 80 to 100 percent, and the temperature approximately 90 to 105 degrees Fahrenheit. Most prior art devices cannot meet or exceed these ideal characteristics. The flow rate of many prior devices is well below 20 liters per minute. Commonly, the flow rate of prior devices has been generally 12 to 14 liters per minute. Most of these devices generally operate by forcing the gas through the humidification material, thereby requiring a high degree of pressure. This increased pressure reduces the flow rate of the gas even further.

SUMMARY OF INVENTION

One aspect of the present invention regards a gas humidification apparatus that includes an inlet, a humidification device in fluid communication with the inlet, the humidification device having a humidification material that readily absorbs moisture and readily releases moisture when exposed to a dry environment, wherein the humidification material has a configuration that generates turbulence in a gas as it passes over a surface of the humidification material and an outlet in fluid communication with the humidification device.

A second aspect of the present invention regards a gas humidification apparatus that includes an inlet, a humidification device in fluid communication with the inlet, the humidification device having a humidification material that readily absorbs moisture and readily releases moisture when exposed to a dry environment, wherein the humidification material is placed within a shell that has a configuration that generates turbulence in a gas as it passes over a surface of the shell and an outlet in fluid communication with the humidification device.

A third aspect of the present invention regards a gas humidification apparatus that includes an inlet, a humidification device in fluid communication with the inlet, the humidification device having a heater housing that includes a heater and a plurality of openings. A humidification material that readily absorbs moisture and readily releases moisture when exposed to a dry environment and an outlet in fluid communication with the humidification device.

A fourth aspect of the present invention regards a gas humidification apparatus that includes inlet means for supplying a gas, turbulence means for generating turbulence in the gas and outlet means for expelling the turbulent gas from the gas humidification apparatus.

A fifth aspect of the present invention regards a method of humidifying a gas that includes supplying a gas to a surface of a humidification material that readily absorbs moisture and readily releases moisture when exposed to a dry environment and generating turbulence in gas as it passes over the surface of the humidification material.

A sixth aspect of the present invention regards a method of humidifying a gas that includes warming a gas, humidifying the gas and placing a catheter in fluid communication with the gas during the humidifying.

A seventh aspect of the present invention regards a gas apparatus that includes an inlet, a heater in fluid communication with the inlet and a temperature sensor for measuring a temperature of a gas that flows within the gas apparatus in an indirect manner.

An eighth aspect of the present invention regards a method of humidifying a gas that includes warming a gas, humidifying the gas and flowing the gas over a surface of a humidifier.

Each of the above aspects provides the advantage of supplying a patient with warmed and/or humidified gas at or near preferred rates, humidity and/or temperature.

The foregoing and other features and advantages of the invention will become further apparent from the following detailed description of the presently preferred embodiments, read in conjunction with the accompanying drawings.

BRIEF DESCRIPTION OF SEVERAL VIEWS OF THE DRAWINGS

FIG. 1 shows a first embodiment of a gas warmer and/or humidifier apparatus according to the present invention;

FIG. 2 shows a second embodiment of a gas warmer and/or humidifier apparatus according to the present invention having a plurality of baffles in the shell;

FIG. 3 shows a third embodiment of a gas warmer and/or humidifier apparatus according to the present invention having an external temperature or humidity sensor;

FIG. 4 shows a cross section perspective view of a gas warmer and/or humidifier apparatus;

DETAILED DESCRIPTION OF THE DRAWINGS

Figure 5:
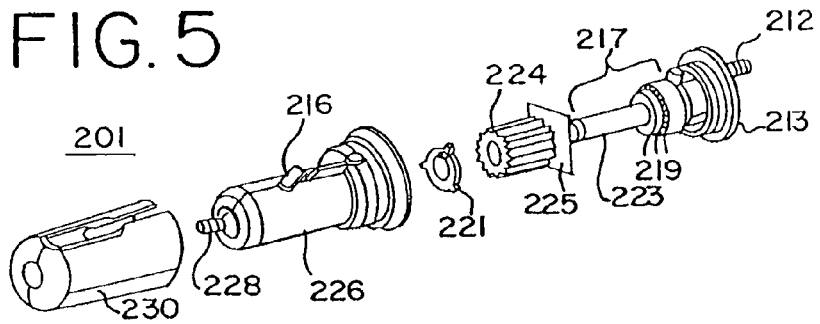
FIG. 5 shows a perspective exploded view of a fourth embodiment of gas humidification apparatus according to the present invention.
Figure 6:
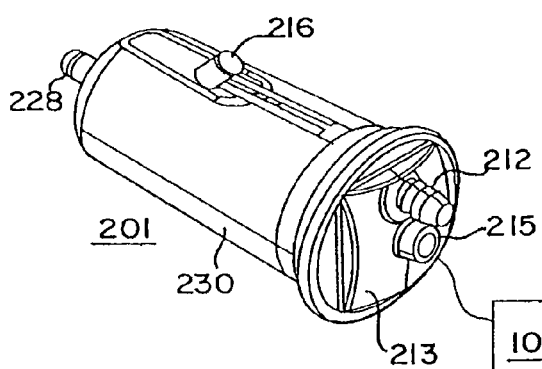
FIG. 6 shows a right top side perspective view of the gas humidification apparatus of FIG. 5.
Figure 7:
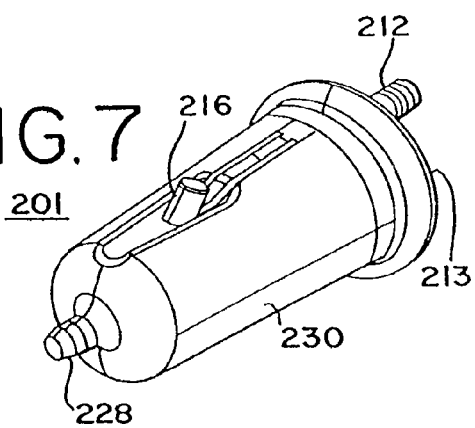
FIG. 7 shows a right bottom side perspective view of the gas humidification apparatus of FIG. 5.
Figure 9:
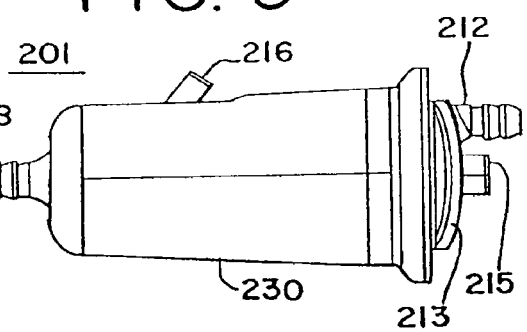
FIG. 9 shows a right side view of the gas humidification apparatus of FIG. 5.
Figure 8:
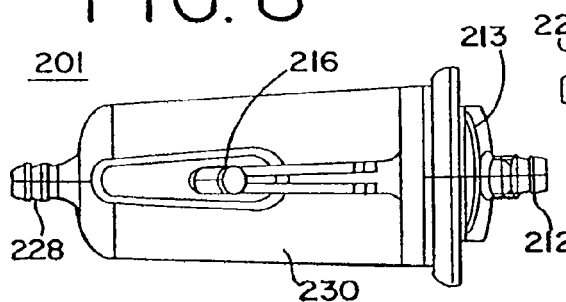
FIG. 8 shows a top view of the gas humidification apparatus of FIG. 5.
Figure 10:
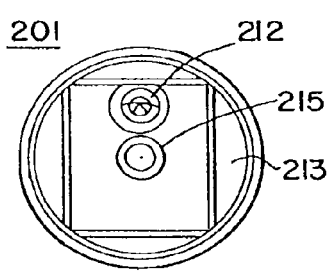
FIG. 10 shows a front view of the gas humidification apparatus of FIG. 5.

FIG. 1 shows one embodiment of the gas warmer and humidification apparatus. FIG. 1 shows the apparatus used in conjunction with an insufflation device. FIGS. 1-3 show the apparatus 1 associated with the insufflation tubing 10. In a preferred embodiment, the apparatus is located downstream from the gas source for the insufflation device where downstream refers to a location closer to output of the insufflation tubing 10 or a patient. The apparatus 1 has an upstream end located nearer to the gas source and a downstream end located closer to the patient. The gas warmer and humidifier apparatus 1 may be constructed as a re-useable or disposable product.

As shown in FIG. 1, in one embodiment, a gas inlet port 12 is located at an upstream end of the apparatus 1 and associable with the insulation tubing 10. A plurality of plugs 14 may also be located at the upstream end of the apparatus 1. The plugs 14 may be male leads for association with the heater 18 and/or a thermocouple and/or other suitable sensing devices. It is to be understood that the location at the upstream end is variable and other locations consistent with the characteristics of the plugs 14 are envisioned.

As shown in FIGS. 1-3, the general arrangement of one embodiment of the apparatus 1 follows. The apparatus 1 includes a heater 18. Surrounding the heater 18 is a core 20. The core 20 maintains the heater 18 in a significantly watertight environment. About the core 20 is a humidification material 24. The humidification material 24 generally envelops the entire core 20. The humidification material 24 may only partially envelop the core 20 as well. A shell 26, acting as a housing, surrounds humidification material 24. At the downstream end of the apparatus 1 may be a gas outlet 28 associable with a downstream portion of the insufflation tube 10.

The heater 18 of the above embodiment may include a conventional cartridge heater, a heat generating wire, a light bulb, or other heat generating device capable of creating an elevated temperature that can radiate from the surface of the heater. As shown in FIG. 1, the heater 18 is insertable within a core 20 of non-conductive material. In further embodiments, as shown in FIG. 2, the heater 18 and plugs 14 are molded into a single assembly that is then molded with the core 20 to make a single unit.

The heater 18 can be a metal structure with integral sensing elements or external sensing elements. It can also be molded of a high temperature resistant plastic. Either the metal or the plastic heater 18 is disposable, although the lower cost of the plastic heater 18 may better suit it as a disposable heater 18. Further, the disposability or re-usability of the apparatus 1 aids in maintaining the apparatus 1 sterile for any purposes that may require a sterile apparatus 1.

Figure 14:
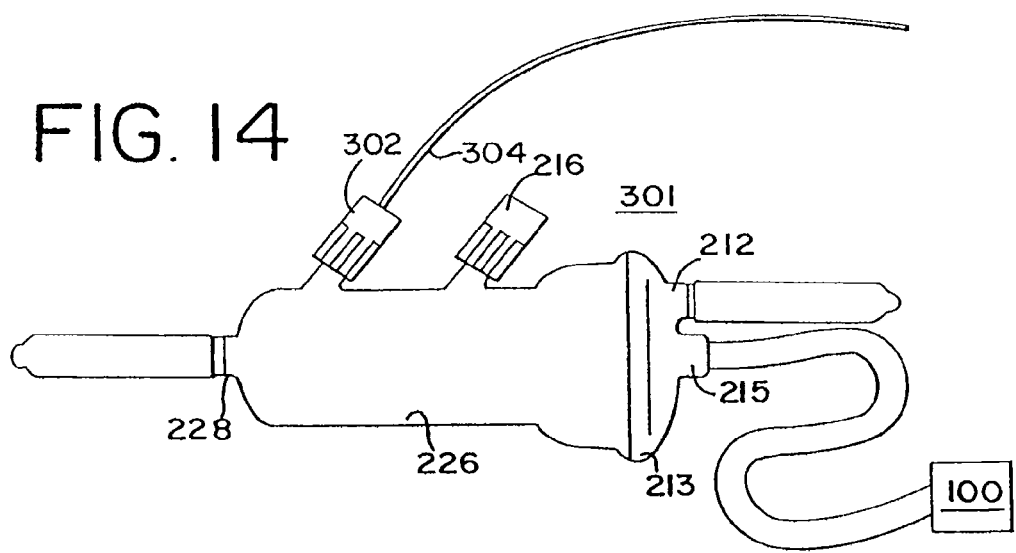
FIG. 14 shows a side view of the gas humidification apparatus of FIG. 13.
Figure 15:
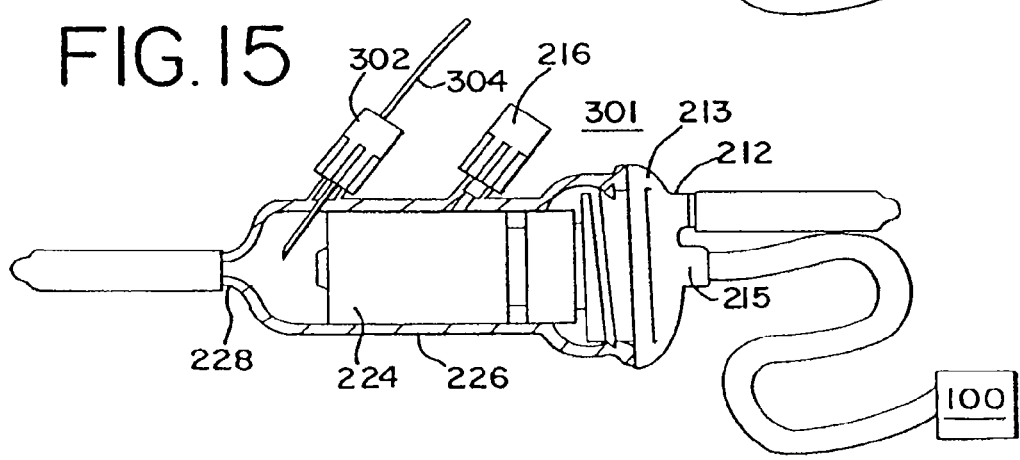
FIG. 15 shows a partially exposed side view of the gas humidification apparatus of FIG. 13.
Figure 16:
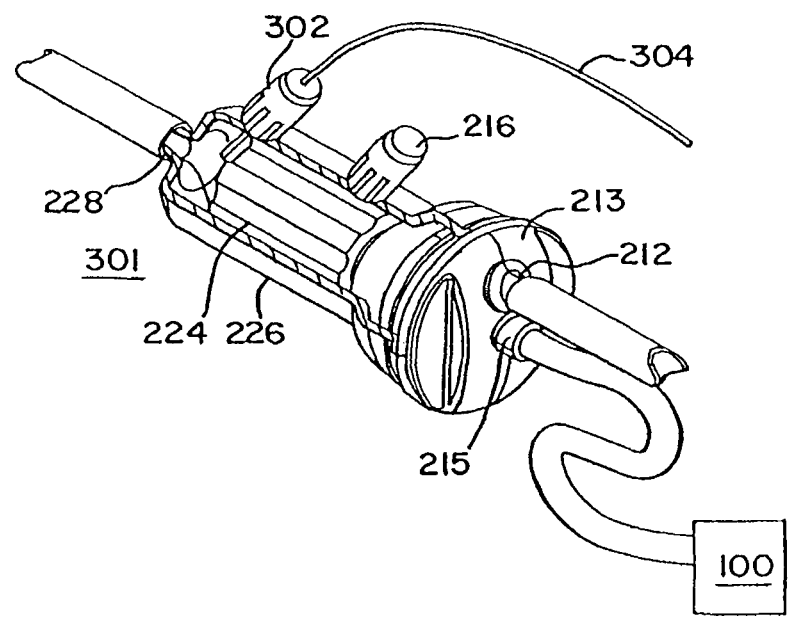
FIG. 16 shows a right front side and partially exposed perspective view of the gas humidification apparatus of FIG. 13.
Figure 17:
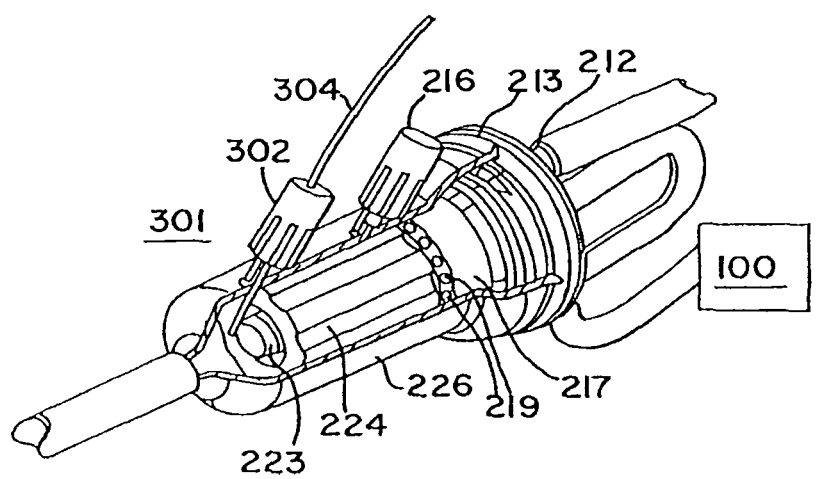
FIG. 17 shows a right rear side and partially exposed perspective view of the gas humidification apparatus of FIG. 13.
Figure 18:
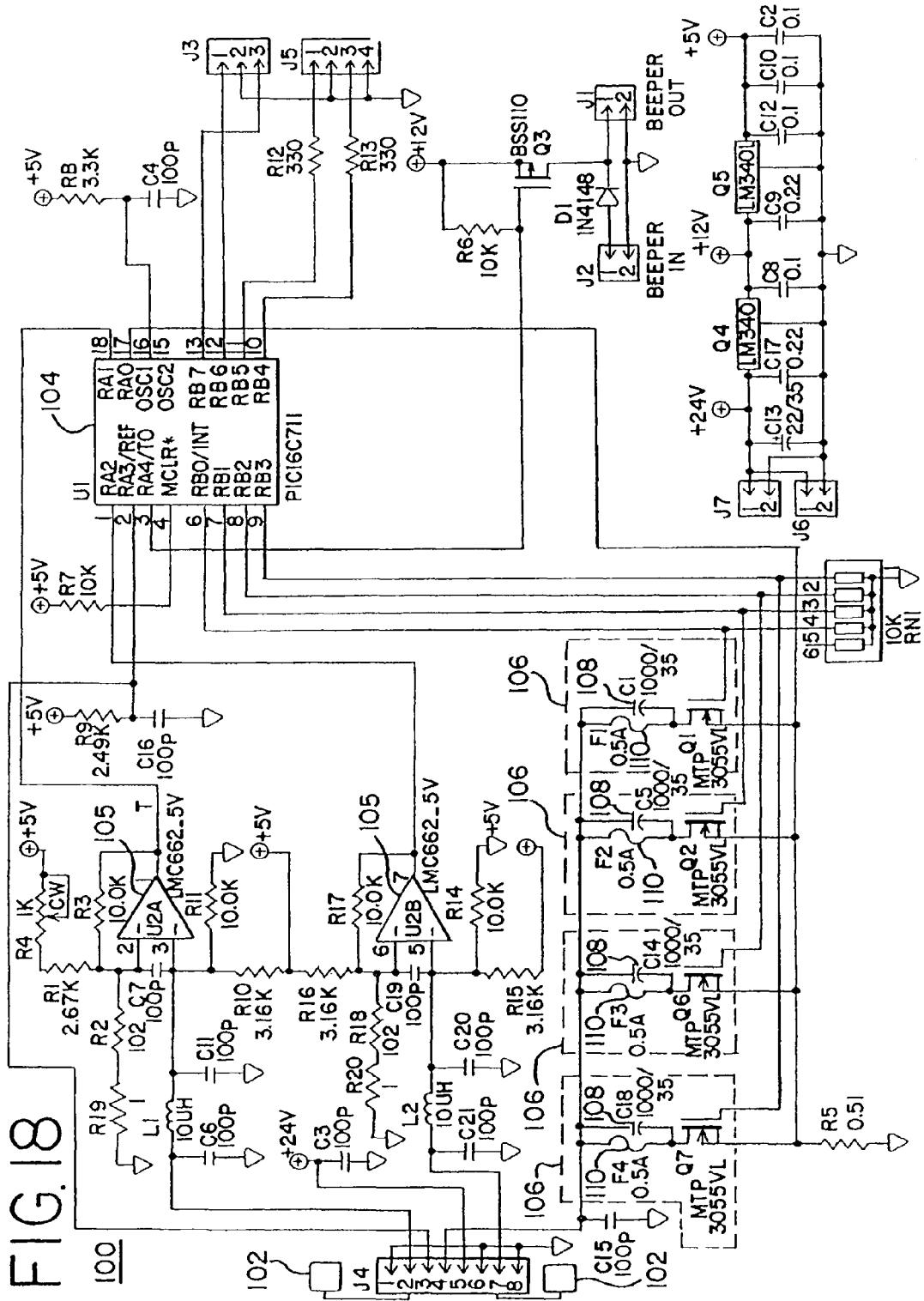
FIG. 18 shows a circuit diagram of heating circuit that can be used with the gas humidification apparatus/gas warmer and/or heater apparatus of FIGS. 1-17.

In a preferred embodiment, the heater 18 has approximately 36 watts of power although heaters 18 with other wattage, such as between 10 watts and 50 watts, can also be used. The heater 18 typically is approximately 1 to 5 inches long, preferably approximately 1½ to 3 inches long, but other sizes can be used depending on the physical size of the other components, and the amount of humidity to be generated. As shown in FIGS. 14 and 18, the heater 18 may be connected to control circuitry 100 controls the amount of heat and rate of heat generated by the heater 18. As shown in FIG. 18, the control circuitry 100 includes one or more temperature sensors 102 and a control system 104 to regulate the degree of energy supplied to the heater 18 by modulating the current supplied to the heater via turning on/off the current and raising or lowering the current. In the case of using two temperature sensors 102, the temperature sensors 102 each independently measure the temperature of the core 20. The temperature signals from temperature sensors 102 are continuously fed to amplifiers 105. The two signals are compared with each other and if it is determined that the difference between the signals reaches or exceeds a predetermined level, such as 5° C., then the control system 104 turns off the current drivers 106 and the current supplied to the heater 18. The current drivers 106 are turned off because reaching or exceeding the predetermined level denotes that one or both of the sensors 102 are defective and need to be replaced.

Assuming that the sensors 102 are not deemed defective, the control system 104 includes four identical current drivers 106 that are in parallel with one another as shown in FIG. 18. Each driver 106 provides an output that is identical with the outputs of the other three drivers 106. The control system 104 will drive each of the outputs of the current drivers 106 with approximately a 25% duty cycle wave shape. The four drivers combined will provide approximately 100% drive to the heater 18. Each driver 106 includes a capacitor 108 of 1000 μF in parallel with a fuse 110. The capacitors 108 direct the current during its respective 25% duty cycle away from its corresponding fuse 110. In the event that a single driver 106 fails, allowing continuous current flow, the corresponding capacitor 108 will charge up and allow current to flow through the corresponding fuse 110. In less than approximately 2 seconds, the fuse 110 in the driver circuit 106 will create an open circuit, thus preventing uncontrolled current to flow to the heater 18.

In one embodiment, the apparatus 1 can have wiring to the heater 18 permanently attached. In another embodiment shown in FIG. 1, the apparatus 1 can have wiring to the heater 18 constructed with an integral connector that can be molded into the apparatus 1 or connected/disconnected via a one time use tab connection system. In yet another embodiment, the apparatus 1 can have wiring to the heater 18 with the terminations molded into a natural connector, so that the cabling can be plugged into it, reducing its cost. The electronic wiring used to provide power and to measure the temperature or humidity can be wired directly to the active elements and over molded. In the preferred embodiment, the output wires will be molded or inserted into the shell 26 in order to make the cord detachable from the apparatus 1.

The heater 18 may be controlled by conventional heater controllers as are available on the market, such as those made by Watlow. Controllers typically are designed to work with temperature sensing devices such as thermocouples resistance temperature detectors (RTD's) and or thermistors.

Optionally, in further embodiments, the apparatus 1 can be provided with additional circuitry to measure humidity using a humidity sensor. Humidity sensors are available through Omega Engineering located in Atlanta, Ga., which can supply both the sensor and circuitry for reading and display. Additionally, optionally, the temperature of the gas and the humidity of the gas could be displayed with additional circuitry. A remote power unit, part of the insufflator, or part of any other device used in the Operating Room associated with endoscopic procedures could provide the additional circuitry to display this information. Based on the readings, adjustments could be made on the amount of moisture fed to the humidification material 24, or how much heat should be applied, or both.

In one embodiment, control could also be tied to the insufflator to supply the circuitry mentioned above. By monitoring characteristics in temperature, gas volume used, gas flow rate and/or humidity readings, the insufflator could dynamically control the variables to maintain optimum conditions.

The core 20 may be made of, but not limited to, plastic or a sheet metal. Some of the plastics that may be used for the core 20 include polycarbonate, Ryton™, Vespel™, or any of the high temperature plastics. A sheet metal such as aluminum coated with a non-conductive substance may also be used for the core 20.

As shown in FIG. 1, the apparatus 1 includes a humidification material 24. The humidification material 24 both readily absorbs moisture and readily releases it when exposed to a dry environment. Materials such as nylon and cotton are just a few of the many commercially available fibers that can meet these requirements. The humidification material 24 can have a tubular inside and outside surface. Tubular refers to a smooth surface. Yet, it is envisioned in further embodiments that the humidification material 24 may have a patterned or varying 15 degrees of a non-smooth surface.

As shown in FIG. 4, the humidification material 24 used in the preferred embodiment has a smooth inner surface and a serrated or star-like shaped outer surface to maximize surface area in the shortest possible linear space. FIG. 4 shows the preferred embodiment including a first and a second section of the humidification material 24. Each section of the humidification material 24 is approximately an inch long with an inner channel in intimate contact with the heater 18. Each of these serrated sections is slid over the core 20 that contains the heater 18. Preferably, a ¼ inch gap should be between the serrated sections. In one embodiment, a plastic spacer may be inserted between the serrated sections to provide the gap. In a preferred embodiment, the first and second serrated sections should be set out of phase with each other to force turbulence of the gas and increase the surface area of the material as it passes over the sections. Note that the first and second serrated sections can be formed from a single serrated material by cutting the single serrated material so that the two serrated sections are formed. After cutting, the two serrated sections are rotated relative to one another until the desired phase difference between the two sections is achieved.

The flow of $CO_2$ gas over the absorbent material is affected by the shape of the absorbent material and/or the channel within the shell 26. In one embodiment, the absorbent humidification material 24 may be cylindrically shaped and surrounded by a coil used to direct the flow of $CO_2$ gas. As the $CO_2$ gas travels through the windings of the coil, warmth and humidity are transferred to the $CO_2$ gas. The external surfaces of the coil rest against the inside of the shell 26 forming a seal that forces the $CO_2$ gas to travel through or within the coil windings.

Other shapes and sizes can be used for the humidification material 24. Manufacturers of this humidification material 24 are Pall Medical located in East Hills, N.Y. and Filtrona Richmond Inc. located in Richmond, Va.

The encased heater 18 elevates the temperature of the humidification material 24 thereby elevating the temperature of the moisture it contains. The elevated temperature of the moisture leads to the creation of a vapor absorbed into the gas as it flows over the humidification material 24. Preferably, the humidification material 24 has a configuration that presents a high surface area to the direction of gas flow to allow increased opportunity for the moisture to evaporate into the gas thereby humidifying the gas.

In a further embodiment, shown for example in FIG. 2, turbulence of the gas is created by the interior of the shell 26 covering the humidification material 24 and heater 18 having a surface area that is of an irregular pattern or texture. This turbulence may be created using a variety of structures. These structures may be located, for example, on or as part of the shell 26 or humidification material 24. Further example of a structure for creating turbulence may be a spiral barrier. In additional embodiments, other structures may be incorporated, for example, by being either attached to the humidification material 24 or interior of the shell 26 of the apparatus 1.

The moisture applied to the humidification material 24 can contain medications or additives that will evaporate and be carried along in the humidified gas to the patient. Levels of medication and/or fluid in the gas can be controlled by timed evaporation and adsorption rates. Fluid could be infused by syringe, gravity feed through tubing, or by any number of pumps, to retain proper saturation levels.

The apparatus 1 will have a port 16 for the infusion of fluid for the production of moisture. Moisture may include sterile water, medication, or a mixture of fluids required for merely humidification or dispensing of medication. The port 16 can be of the standard injection port used typically in the medical industry, a valve, or any other device, which can open or close allowing for the entrance of the fluid.

The apparatus 1 includes one or more temperature sensing devices (not shown) to regulate the heater 18. Each temperature-sensing device can be a resistive temperature device (RTD), a thermister, or a thermocouple. In the preferred embodiment, a K type thermocouple is embedded inside the heater 18 to measure its temperature. Any number of heater controller manufacturers such as Watlow or Hot Watt can provide the temperature sensing and control device. As shown in FIG. 1, the shell 26 is an oblong tube having an internal channel, but any shape that will accommodate the internal elements of the device is acceptable. In the preferred embodiment, the internal channel of the shell 26 will be smooth. In a further embodiment, any form of surface irregularity to promote turbulence without flow restriction is acceptable for the 15 internal channel of the shell 26. The shell 26 has an output opening 28 and an input opening 12 for the gas. The shell 26 additionally has a fluid fill port 16 for the infusion of fluid. Although, other methods of inserting the appropriate fluid or medicine in the shell 26 are possible.

Overall length of the preferred embodiment will be between 3½ and 4 inches. Preferably, the apparatus 1 will weigh approximately four ounces. The shell 26 can be made of any suitable material, for example, metal or plastic.

In additional embodiments, as shown in FIG. 3, a humidity sensor 34 may be included in the apparatus 1. Appropriate humidity sensors 34 can be obtained from Omega Corporation located in Atlanta, Ga.

Optionally, in further embodiments, in addition to the temperature sensing device described above, an external temperature sensing device 32 can be inserted in the insufflation tubing 10 just outside of the gas outlet 28. The same types of temperature sensing devices internal to the apparatus 1 as described above can be used. This device 32 measures the downstream temperature of the gas.

The temperature of the gas is related to the temperature of the heater 18. The temperature sensing device located within the heater 18 measures the temperature of the heater 18. The temperature of the gas is not directly measured. Rather, the resulting temperature of the gas correlates to the temperature of the heater.

The warmed and humidified gas leaves the apparatus 1 through a gas outlet 28. The gas outlet may be a series of holes. The gas then enters the insufflation tubing 10 for possible delivery to a patient.

Another embodiment of a gas humidification apparatus is shown in FIGS. 5-12. In a manner similar to the devices of FIGS. 1-4, the gas humidification apparatus 201 can be used in conjunction with an insufflation device. In particular the gas humidification apparatus 201 is located downstream from a gas source for the insufflation device. The gas humidification apparatus 201 may be constructed as a re-useable or disposable product.

As shown in FIGS. 5, 6, 9 and 10, a gas inlet port 212 is attached through a side portion of a front cap 213 of the gas humidification apparatus 201. In addition, an inlet port 215 is attached through a central portion of the front cap 213. The inlet port 215 allows for electrical components and wiring to be inserted into the gas humidification apparatus 201. The gas humidification apparatus 201 can be modified so that the ports 212 and 215 are interchanged with one another.

As shown in FIG. 5, the cap 213 includes an annular metallic heater housing 217 that is attached thereto. The heater housing 217 is in fluid communication with the gas inlet port 212. The heater housing 217 contains a heater cartridge that is well known in the art. When activated the heater cartridge heats up the interior and body of the heater housing 217 so that gases within and outside the heater housing 217 are heated. The heater housing 217 also includes a plurality of circular holes 219 having a diameter of approximately 0.1" (0.254 cm). Other shapes and sizes for the holes 219 are possible, such as triangular and square shaped openings. When gas flows into the gas humidification apparatus 201 via the gas inlet port 212, the gas flows into the heater housing 217, where it is heated if necessary, and then flows out of the holes 219. As shown in FIG. 5, there are approximately sixteen holes 219 that are arranged equidistantly from one another along an annular ring. The holes 219 of the heater housing 217 improve the rate of heating of the gas within the gas humidification apparatus 201 and create turbulence for the gas flowing within the gas humidification apparatus 201.

Two of the holes 219 preferably have their own RTD sensor. These sensors operate in the same manner as the temperature sensors for the embodiments of FIGS. 1-4. In particular, the temperature measured by the two sensors are compared with one another to determine if one or both of the sensory is defective.

As shown in FIG. 5, a rear cylindrical portion 223 of the heater housing 217 is snugly inserted into a cylindrical central opening of a humidification material 224 that is preferably made of the same material as the humidification materials 24 described previously with respect to FIGS. 1-4. A washer 221 is fitted over the rear portion 223 and abuts against the rear face of the humidification material 224 and acts as a stop in that it prevents the humidification material 224 from slipping off of the rear portion 223 and being wedged into an outlet 228.

In an alternative embodiment, the gas humidification apparatus 201 can further include a plate 225 positioned between the front or proximal end of the humidification material 224 and the heater housing 217. Since the holes 219 face the front end of the humidification material 224, the plate 225 allows the gas to flow along the exposed side of the humidification material. Note that the gas will flow along the side of the humidification material with or without the presence of the plate 225.

Figure 12:
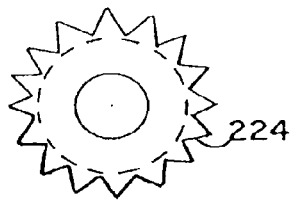
FIG. 12 shows a top view of an embodiment of a humidification material to be used with the gas humidification apparatus of FIG. 5.
Figure 11:
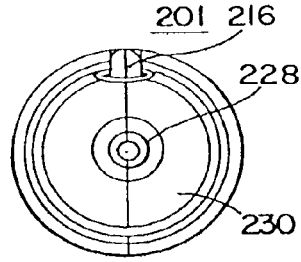
FIG. 11 shows a rear side perspective view of the gas humidification apparatus of FIG. 5.
Figure 13:
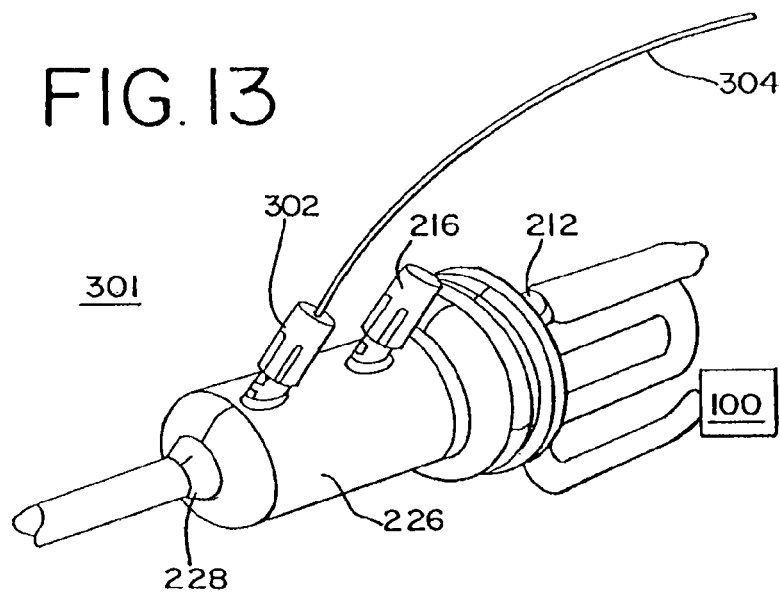
FIG. 13 shows a perspective view of a fifth embodiment of gas humidification apparatus according to the present invention.

As shown in FIG. 12, the humidification material 224 has a star-like pattern with ten to twelve points that aid in generating turbulence in the gas within the gas humidification apparatus 201 in a similar manner that the humidification material 24 of FIGS. 1 and 4 do.

In an alternative embodiment, a second humidification material 224 may be spaced from the first humidification material by a spacer and out of phase with the first humidification material in the same manner as described previously with respect to the embodiment of FIGS. 1 and 4.

As shown in FIG. 5, the assembled humidification material 224 and washer 221 and the inlet port 215 and the heater housing 217 are inserted into a housing or shell 226. After insertion, the front cap 213 is screwed on or snap fit onto the heater housing 217. The housing 226 is made of a suitable material, such as plastic or metal, and has a downstream outlet 228 that allows the gas to flow outside of the housing 226.

As shown in FIGS. 5-9 and 11, the housing 226 includes a port 216 that allows fluid to be infused by syringe, gravity feed through tubing, or by any number of pumps, to the humidification material 224. The fluids infused may include sterile water, medication, or a mixture of fluids required for merely humidification or dispensing of medication. The interior end of the port 216 is positioned so that infused fluids drip into the housing 226 and are soaked up by the entire humidification material 224 by capillary action. The port 216 is similar to the port 16 described previously with respect to the embodiments of FIGS. 1-4.

As shown in FIGS. 5-9, the housing 226 is inserted into a sleeve or shroud 230 so that the port 216 is slid along a slit 232 formed in the sleeve 230 and the outlet 228 extends through a rear opening 234 of the sleeve 230. The sleeve 230 is snap fit to the housing 226. The sleeve 230 is made of a thermal insulation material that retains the heat within the housing 226 so that a person can handle the sleeve 230 without fear of being exposed to excessive heat and without significantly heating up the ambient atmosphere.

Note that the sleeve 230, the housing 226 and the humidification material 224 may be disposable while the cap 213 and its attached heater housing 217 may be reusable.

The gas humidification apparatus 201 may include the temperature sensors, humidity sensors and control circuitry previously described with respect to the embodiments of FIGS. 14 and 18 so that the temperature and humidity of the gas flowing within the apparatus and delivered to a patient via outlet 228 is controlled.

Another embodiment of a gas humidification apparatus is shown in FIGS. 13-17. The gas humidification apparatus 301 essentially has the same structure as the gas humidification apparatus 201 of FIGS. 5-12 and so like components will be designated with like numerals. One difference is that a second port 302 is added to the housing 226. The second port 302 is positioned between the humidification material 224 and the outlet 228 so as to allow a distal end of a catheter 304 to be inserted into the port 302. Depending on the intended material to be delivered to the patient, the distal end of the catheter 304 may be positioned within the port 302, within the interior of the gas humidification apparatus 301 or within a tube attached to the outlet 228 and in fluid communication with a section of a patient, or within the section of the patient. An example of a catheter that can be inserted into the gas humidification apparatus 201 is the catheter described in U.S. Pat. No. 5,964,223, the entire contents of which are incorporated herein by reference. Other devices can be inserted into the port 302 in a similar manner as described above with respect to catheter 304, such as a lumen and an endoscope. Furthermore, gases, liquids, aerosols and medicines may be conveyed to a patient by a tube or other know dispensing devices inserted through the port 302 and exiting out of the outlet 228 into the patient. Note that the materials dispensed into the port 302 by the above-mentioned dispensing devices may have properties that raise the humidity of the gas within the interior of the gas humidification apparatus 301.

The gas humidification apparatus 301 may include the temperature sensors, humidity sensors and control circuitry previously described with respect to the embodiments of FIGS. 1-4 and 18 so that the temperature and humidity of the gas flowing within the apparatus and delivered to a patient is controlled.

In each of the devices for humidifying and/or warming a gas described previously with respect to FIGS. 1-18, it is desired that the flowing gas achieves a humidity that ranges from approximately 80 to 100 percent humidity and achieves a temperature that ranges from approximately 90 to 105 degrees Fahrenheit at a constant flow rate of approximately 20 liters per minute.

The embodiments of the invention disclosed herein are presently considered to be preferred, various changes and modifications can be made without departing from the spirit and scope of the invention. As noted, the discussion above is descriptive, illustrative and exemplary and is not to be taken as limiting the scope defined by any appended claims, and all changes that come within the meaning and range of equivalents are intended to be embraced therein.

What is claimed is:

1. A gas apparatus for use in a medical procedure comprising:

a housing defining a chamber having a gas inlet and a gas outlet;

a heater for warming a gas flowing through the chamber;

a port in fluid communication with the chamber; and a dispensing device inserted within the port for delivering water in aerosol form to warmed gas as it exits the gas outlet.

2. The gas apparatus of claim 1, wherein a distal end of the dispensing device is positioned within a gas flow lumen between the chamber and a patient.

3. The gas apparatus of claim 1, wherein a distal end of the dispensing device is positioned within an interior of the gas apparatus.

4. A method for using a gas apparatus in a medical procedure, the method comprising:

receiving a gas at a gas inlet of a chamber, the chamber defined by a housing of the gas apparatus;

warming the gas with a heater of the gas apparatus as the gas flows through the chamber to a gas outlet of the chamber; and delivering, with a dispensing device, water in aerosol form to warmed gas as it exits the gas outlet.

5. The method of claim 4, further comprising:

humidifying the gas as the gas flows through the chamber in at least two gas flow chambers of a humidification material positioned adjacent to the heater in the chamber;

wherein the medical procedure is a laparoscopic procedure.

6. The method of claim 5, further comprising:

receiving gas from the gas inlet at a heater housing of the heater, where the heater housing is in fluid communication with the gas inlet.

7. The method of claim 6, wherein the heater housing comprises a plurality of holes through which the gas exits the heater.

8. The method of claim 7, further comprising:

directing the gas exiting the heater into the at least two gas flow chambers of the humidification material using the plurality of holes of the heater housing.

9. The method of claim 5, wherein humidifying the gas as the gas flows through the chamber in at least two gas flow chambers of the humidification material comprises:

humidifying the gas as the gas flows through eight gas flow channels of the humidification material.

10. The gas apparatus of claim 1, further comprising:

a humidification material adjacent to the heater and comprising at least two gas flow channels for flowing gas over the humidification material;

wherein the medical procedure is a laparoscopic procedure.

11. The gas apparatus of claim 10, wherein the heater comprises a heater housing in fluid communication with the gas inlet.

12. The apparatus of claim 11, wherein the heater housing comprises a plurality of holes.

13. The apparatus of claim 10, wherein the humidification material comprises a cylindrical central opening.

14. The apparatus of claim 10, wherein the heater comprises a cylindrical portion for insertion into a cylindrical central opening.

* * * * *